United States Patent [19]

Charney et al.

[11] Patent Number: 4,576,454
[45] Date of Patent: Mar. 18, 1986

[54] EYE FATIGUE SIMULATOR FOR OPTOMETRY

[75] Inventors: Gregory S. Charney; Terrance D. Hohner, both of Portland; Cosmo Salibello, Forest Grove, all of Oreg.

[73] Assignee: Terrance D. Hohner, Portland, Oreg.

[21] Appl. No.: 555,036

[22] Filed: Nov. 22, 1983

[51] Int. Cl.4 ............................................. A61B 3/02
[52] U.S. Cl. ..................................... 351/243; 351/234; 351/222
[58] Field of Search ............... 351/233, 234, 235, 222, 351/243

[56] References Cited

U.S. PATENT DOCUMENTS

| | | | |
|---|---|---|---|
| 2,282,494 | 5/1942 | Potter | 351/233 |
| 4,212,520 | 7/1980 | Klimsa | 351/243 |
| 4,421,392 | 12/1983 | Crick | 351/243 X |

Primary Examiner—Rodney B. Bovernick
Attorney, Agent, or Firm—Robert L. Harrington

[57] ABSTRACT

A simulation card for simulating the eye fatigue of a user of a display screen. The simulation card is adapted to mount in front of a lens changing apparatus. An opening in the card permits the eye doctor to examine the patients eyes while the patient focuses on images that surround the opening. A light source behind the card projects through a diffuser screen e.g., frosted "Mylar" plastic film to simulate, on the viewing screen, the images of a display screen.

5 Claims, 4 Drawing Figures

EYE FATIGUE SIMULATOR FOR OPTOMETRY

FIELD OF INVENTION

This invention relates to a device that induces eye muscle utilization that simulates e.g., the conditions for users of Cathode Ray Tube Display Screens.

BACKGROUND OF INVENTION

The use of Cathode Ray Tubes and similar equipment where light projected images are displayed on display screens is wide spread throughout industry and many millions of users sit day after day hours on end before display screens feeding information into and taking information out of a computer based system. For long periods of time during such use, the user focuses his eyes on relatively small areas of the display screen. The use of the display screen generates stress on the eye muscles that are peculiar to display screen observation.

The display screen is generally about 20 inches from the users eyes and that distance remains relatively constant throughout. Whereas the distance is set up to be somewhat ideal for the user, because there is very little variation, the same eye muscles are in constant use. This causes a strain on those eye muscles not unlike the strain that occurs e.g., in an arm muscle when a light object is held in an extended position for a long period of time.

Also, the images that are displayed on the screen are produced by patterns of dots or line segments. The images thus produced are not crisp and to the eye are slightly out of focus. The images can be read clearly enough but the eye muscles of accommodation are constantly trying to bring the images into focus. This causes a further eye strain phenomenon which in combination with the stationary muscle strain previously explained, creates an eye problem for the video display screen user that is atypical of eye problems encountered for non-users.

The process used by eye doctors to determine the spectacle correction requirements of the typical patient is quite basic. An apparatus is placed in front of the user's eyes that enables the doctor to rapidly change a wide selection of lenses through which the patient is viewing. Images printed on a test card are placed some distance from the patient and as the patient focuses on these images, the doctor assesses the status of the muscles inside the patients eyes with the use of a retinoscope. He can thus determine which combination of lenses is best suited for the patient i.e., when the eye muscles are at a generally relaxed state.

Whereas the process and the equipment currently available are quite satisfactory for prescribing corrective lenses for the average eye problem, such is not satisfactory for correcting the eye problems of the display screen user. The muscles that have created the eye problem for the display screen user cannot be examined under stress with this equipment.

As it will be understood, the fitting of corrective lenses is basically one of trial and error which is quite satisfactory as long as the problem can be simulated in the doctors office and lenses rapidly changed until the lens combination which is most suitable is found to correct the problem. Without the problem simulator (and as heretofore required for display screen users), the same trial and error method involves the doctors educated guess at what lens correction may work best and having the patient go back to his work station to try it out. This is time consuming, expensive, inaccurate and generally unsatisfactory.

BRIEF DESCRIPTION OF THE INVENTION

The present invention is believed to solve the described problem of fitting corrective lenses to display screen users by providing a device that simulates the eye strain conditions of display screen use. This device can be used in combination with existing eye examination equipment to allow the eye doctor to examine the eye muscles under the simulated conditions and to determine the best corrective lenses for the patient under those conditions.

In brief, the preferred embodiment of the invention includes a card mounted a desired distance forward of the lens changing apparatus e.g., 20 inches forward of the patient's eyes when positioned in the lens changing apparatus. The card may be simply mounted on a rod that is affixed to the apparatus. A swivel arrangement for the rod and/or card enables the eye doctor to move the card in or out of the examination process.

The card has a black or dark (opaque) surface that faces the patient, and a center opening of e.g., one inch diameter. Positioned at equal distance positions around the opening (like numbers on the face of a clock) are images such as letters or numbers, preferably at 5 or more locations. These images are illuminated from behind by a light source projected through the card with the light diffused to simulate the images projected on a display screen. The patient focuses on the images in sequence, under the instruction of the eye doctor, while the doctor examines the patient's focusing response muscles. The doctor then changes the lenses to determine the combination that most relaxes the focusing muscles under these conditions.

DETAILED DESCRIPTION AND DRAWINGS

The invention will be further understood by reference to the following detailed description and to the drawings referred to therein which include:

FIG. 1 schematically illustrates an eye examination procedure utilizing the device of the present invention;

Figure 1:
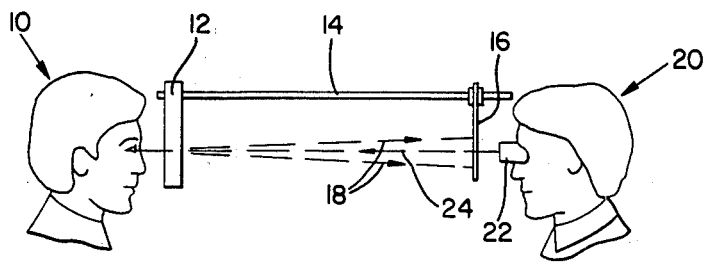

Referring to FIG. 1 of the drawings, a patient 10 is positioned so as to look through a lens changing apparatus 12, typical of the apparatus used by eye doctors in examining a patient's eyes. With this apparatus the doctor has the ability of selectively shifting a combination of lenses into the viewing path of the eye being examined. This apparatus and its use is well known and will not be further explained.

A mounting rod 14 is mounted at one end to the lens changing apparatus 12 and carries at the opposite end a simulation card 16. As will be further explained with reference to FIGS. 2-4, the simulation card has a central opening with images positioned around the opening. While the patient, by instruction, views the images positioned around the opening (indicated by arrows 18) the doctor 20 examines the patient's focusing capability with the use of a retinoscope 22 by looking through the central opening in the simulation card and into the eye (indicated by arrow 24).

Figure 2:
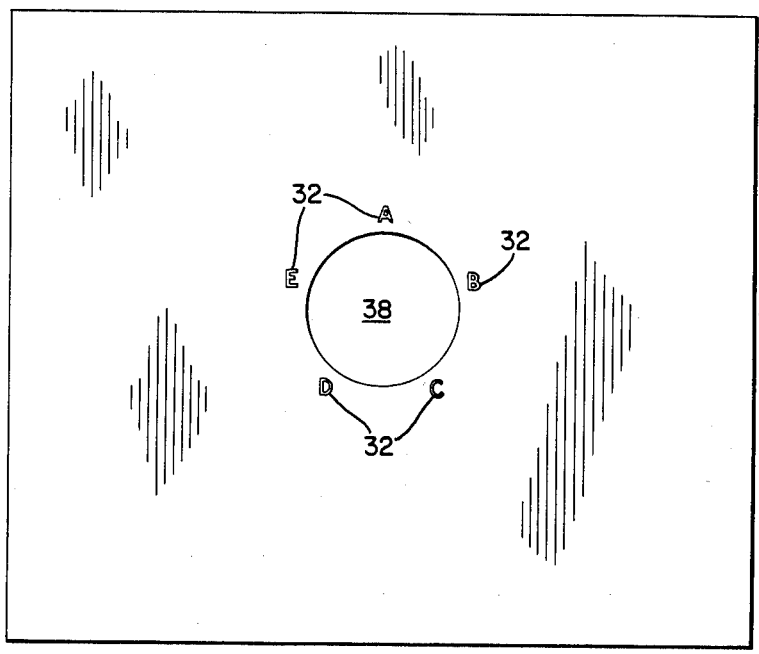
FIG. 2 is the viewing side of a simulation card as used in the device of the present invention.
Figure 3:
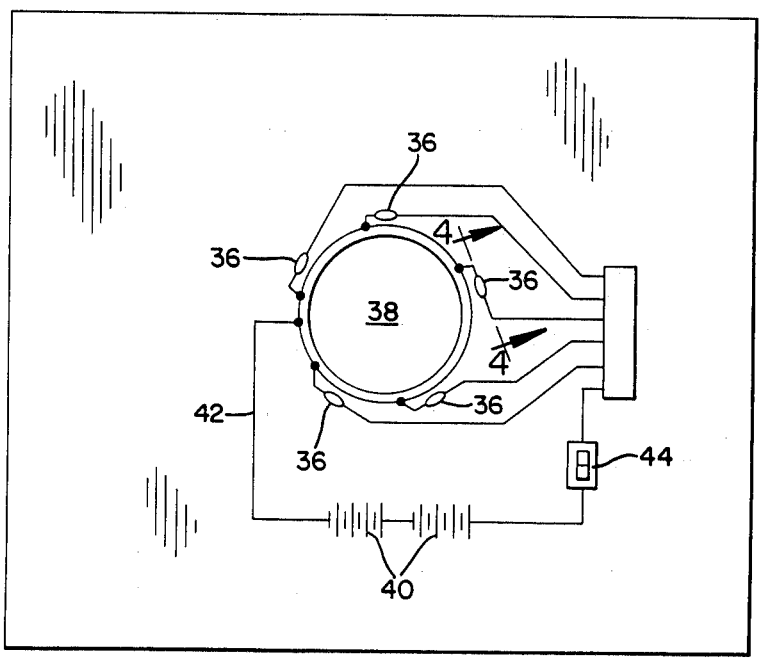
FIG. 3 is the examination side of the simulation card of FIG. 2.
Figure 4:
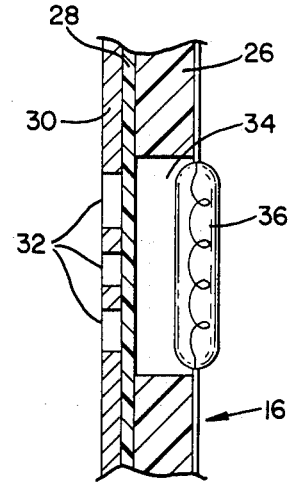
FIG. 4 is a partial section view as taken on section lines 4—4 of FIG. 3.

Reference is now made to FIGS. 2 through 4. The simulation card 16 includes a backing sheet 26 that supports a diffuser screen 28. The diffuser screen is a plastic film e.g., ("Mylar") that is frosted to make it transluscent. A black opaque layer 30 is coated over the diffuser screen e.g., black paint that is painted on the screen.

Images 32 are formed on the viewing side of the card 16 by removing the opaque layer 30 from the image areas (see FIG. 4). The general area 34 of the backing sheet overlying each of the images 32 is also removed. A light source 36 is mounted over the removed areas 34 of the backing sheet 26 on the back side of the card 16. It will be understood that the light rays projected from the light source 36 are directed through the diffuser screen 28 and through the cut out areas of the opaque layer which form the images 32. The light rays are randomly scattered by the diffuser screen so that the images, as they appear to the patient, are "fuzzy", closely duplicating the images projected on a video display screen.

Referring now more specfically to FIG. 2, the simulator card 16 is provided with a central opening 38. Although the size of the opening may vary somewhat, it is desirable that the line of sight of the patient 18 align as closely as practical with the line of sight of the doctor 24 while still allowing the doctor enough of an opening to view the patients eye. An acceptable opening has a one-half inch to two inch diameter with images of a standard commonly known as 20/40 to 20/80 visual acuity, spaced as close as practical to the opening. The number of images can also vary somewhat but it is believed that the best number is five images located equally on the periphery of the opening.

Reference is now made to FIG. 3 which shows the examination side of the card 16 whereat the light source 36 and circuitry therefore are provided. The light sources 36 are light emitting diodes (LED) of green, amber and gray color to simulate the color commonly in use in production display videos. It will be understood that an opening 34 is provided in backing sheet 26 in line with each of the images 32 and that a light emitting diode (light source 36) is positioned at each of the openings 34. As is typical for such circuitry, a power source 40 e.g., batteries conducts power through conductors 42 to each of the light emitting diodes. An on-off switch 44 switches the power to the light emitting diodes as desired by the eye doctor.

PROCESS OF EYE EXAMINATION

The objective of this invention is to simulate for a patient in an examination room setting the eye strain experienced when viewing a display screen on which light projected images are displayed. It is the further objective of this invention to provide a means whereby the eye muscles of the patient can be examined while experiencing such simulated eye strain. This is achieved by mounting a simulation card 16 the same distance from the patients eyes as he would normally be from the display screen e.g., 20 inches forward of the lens changing apparatus 12; by providing images 32 on the card that are generally the same size, color and kind as viewed by the patient on the video display screen; by providing the images 32 slightly distorted or "fuzzy" to thereby induce the focusing muscles to be urging clarity of the images 32; by providing the images in a symetrical pattern over an area that is typical of eye movement patterns when viewing a display screen, e.g., over a circular area one-half inch to two inches in diameter; and by providing a center opening 38 through which an eye doctor 20 can view the focusing response of the eyes to the images.

In general the eye doctor will position the patient with his eyes aligned with a lens changing apparatus 12. A patient's line of sight is directed through the lens positioned in the apparatus as determined by the doctor. The doctor then positions the simulation card on the line of sight with the opening 38 located so as to enable the doctor to examine the eye with the aid of a retinoscope.

The images are lighted by switching on the light emitting diodes which generate the "fuzzy" images previously described. The doctor then instructs the patient to view designated images while assessing the patient's eye focusing. As typical in such examinations, the lenses are changed in the lens changing apparatus until, by diagnosing the eye muscle activity, the doctor determines the most relaxed condition and thus the lens correction desired.

The above described embodiment is of course subject to numerous variations without departing from the scope of the invention. Examples of such variations may include replacement of the manual switch 44 with a gravity actuated mercury switch. The card when pivoted out of the patient's sight line will cause the flow of mercury in the switch to turn the switch off. Conversely, pivoting the card into the patient's sight line turns it on. A further variation may be to control the lighting of the light emitting diodes so that the patients attention is directed to the images in a programmed sequence. These variations are accordingly encompassed by the claims appended hereto.

We claim:

1. A system for simulating the eye fatigue of a video display screen user and for determining the desired corrective lenses for that user comprising; a lens changing apparatus adapted to mount in front of a patient's eyes whereby different lenses can be selectively positioned into the patient's line of sight, a simulation device mounted in spaced relation to the lens changing apparatus and in the patient's line of sight, said simulation device having a viewing surface in the patient's line of sight surrounding a center opening through which the patient's eyes can be examined by an eye doctor, and images formed on the viewing surface adjacent said opening, said simulation device including a multilayer card-like member having a patient viewing side providing said viewing surface, a diffuser screen forming a layer of the member, an opaque coating forming a layer over the screen on the viewing side of the member, and said images provided by the discriminate removal of the opaque coating in the desired image areas to expose the underlying diffuser screen, and a light source on the opposite side of the member for projecting light through the diffuser screen in the image areas to project nonfocused images on said viewing surface simulating the images of a video display screen.

2. A system as defined in claim 1 wherein; the light source is provided by light emitting diodes on the examination side of the card aligned with each of the image areas, and a battery operated self-contained circuitry mounted on the examination side of the card, and a switch contained in the circuitry for selectively electronically activating the light emitting diodes.

3. A system as defined in claim 2 wherein; the mounting means for the card includes pivoting means for pivoting the card into and out of the line of sight of the patient.

4. A system as defined in claim 3 wherein; the switch is gravity operated to activate the light emitting diodes with the card pivoted into the patient's line of sight, and deactivated with the card pivoted out of the patient's line of sight.

5. A method for an eye doctor to examine the eyes of a video display screen user to determine the desired corrective lenses to be used during display screen use which comprises; placing a lens changing apparatus in front of the patient's eyes, placing, at a position forward of the lens changing apparatus, a simulation device having a diffuser screen with light transmitting designated image areas, a center opening and opaque non-designated areas, projecting light through the diffuser screen to form video display simulated images, instructing the user to focus on the images, and examining the reaction of the user's eye muscles through the center opening while changing the lenses to determine the desired lens prescription.

* * * * *